(12) United States Patent
Bödewadt et al.

(10) Patent No.: US 10,092,295 B2
(45) Date of Patent: Oct. 9, 2018

(54) IMPLANTABLE MEDICAL DEVICE WITH TWISTED ELEMENT

(71) Applicant: COOK MEDICAL TECHNOLOGIES LLC, Bloomington, IN (US)

(72) Inventors: Tue Thuren Bödewadt, Solroed Strand (DK); Christina Rauff Hansen, Copenhagen (DK); Kim Møgelvang Jensen, Frederiksberg (DK); Raimo Urban Jensen, Haslev (DK); Erik E. Rasmussen, Slagelse (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 400 days.

(21) Appl. No.: 14/700,327

(22) Filed: Apr. 30, 2015

(65) Prior Publication Data

US 2015/0313603 A1    Nov. 5, 2015

(30) Foreign Application Priority Data

May 1, 2014   (GB) .................................... 1407686.3
Mar. 31, 2015 (EP) .................................... 15275101

(51) Int. Cl.
*A61B 17/12* (2006.01)
*A61F 2/844* (2013.01)
(Continued)

(52) U.S. Cl.
CPC .. *A61B 17/12109* (2013.01); *A61B 17/12031* (2013.01); *A61B 17/12131* (2013.01);
(Continued)

(58) Field of Classification Search
CPC ... A61F 2/01; A61F 2/844; A61F 2/90; A61B 17/12031; A61B 17/12109;
(Continued)

(56) References Cited

U.S. PATENT DOCUMENTS 5,197,984 A   3/1993  Kedem
6,063,113 A   5/2000  Kavteladze et al.
(Continued)

FOREIGN PATENT DOCUMENTS

GB       2514135 A       11/2014
WO    WO 2008/074027 A1   6/2008
WO    WO 2015143432 A1 *  9/2015  ....... A61B 17/12031

OTHER PUBLICATIONS

Examination Report for Application No. GB1407686.3 dated Feb. 5, 2016.
European Search Report for Application No. 15275101.2-1654 dated Aug. 24, 2015.

*Primary Examiner* — Katherine M Shi
*Assistant Examiner* — Brooke Labranche
(74) *Attorney, Agent, or Firm* — Brinks Gilson & Lione

(57) ABSTRACT

A vascular occluder includes a tubular support element and a sleeve of occluding material disposed within the support element. The sleeve is twisted in the support creating a constriction which closes the lumen of the sleeve. The lumen of the sleeve can nevertheless be opened by a guide wire or cannula for over the wire delivery. Once the guide wire or cannula are withdrawn from the sleeve, the sleeve will close again by the action of blood pressure thereon. Blood pressure will act to maintain closing pressure on the sleeve, thereby avoiding or reducing the risk of recanalization.

19 Claims, 3 Drawing Sheets

(51) Int. Cl.
*A61F 2/90* (2013.01)
*A61F 2/01* (2006.01)

(52) U.S. Cl.
CPC .. *A61B 17/12172* (2013.01); *A61B 17/12177* (2013.01); *A61F 2/01* (2013.01); *A61F 2/844* (2013.01); *A61F 2/90* (2013.01); *A61F 2002/011* (2013.01); *A61F 2002/016* (2013.01); *A61F 2002/018* (2013.01); *A61F 2230/001* (2013.01)

(58) Field of Classification Search
CPC ........ A61B 17/12118; A61B 17/12168; A61B 17/12122; A61B 17/12131; A61B 17/12172; A61B 17/12177
See application file for complete search history.

(56) References Cited

U.S. PATENT DOCUMENTS

| | | | |
|---|---|---|---|
| 6,071,292 | A | 6/2000 | Makower et al. |
| 7,445,623 | B2* | 11/2008 | Mialhe ............... A61B 17/0057 600/30 |
| 8,443,808 | B2 | 5/2013 | Brenzel et al. |
| 2003/0153935 | A1 | 8/2003 | Mialhe |
| 2006/0052804 | A1 | 3/2006 | Mialhe |
| 2006/0058820 | A1 | 3/2006 | Mialhe |
| 2007/0208368 | A1* | 9/2007 | Katoh ............... A61B 17/32072 606/198 |
| 2008/0097509 | A1 | 4/2008 | Beyar et al. |
| 2008/0114445 | A1* | 5/2008 | Melsheimer ............... A61F 2/07 623/1.13 |
| 2013/0178750 | A1 | 7/2013 | Sheehan et al. |

* cited by examiner

IMPLANTABLE MEDICAL DEVICE WITH TWISTED ELEMENT

RELATED APPLICATIONS

This application claims the benefit of priority under 35 U.S.C. § 119(a) to European Patent Application No. EP 15275101.2, filed Mar. 31, 2015 and Great Britain Patent Application No. GB 1407686.3, filed on May 1, 2014, both of which are incorporated by reference here in their entirety.

TECHNICAL FIELD

The present invention relates to an implantable medical device, in particular but not exclusively to a vascular occlusion device. The device could also be configured as a filter.

BACKGROUND ART

Vascular occlusion devices are well known in the art and can have many forms. A convenient type of occluder is one which is implanted in the vessel of a patient and is deployable via endoluminal insertion from a remote percutaneous entry point. This type of occlusion device can avoid the need for invasive open surgery, vessel ligation and so on. Some such devices can also be removable from the patient via an endoluminal retrieval procedure once no longer required.

Implantable occlusion devices of this type may either provide instantaneous occlusion of the vessel, principally by creating a physical barrier across the vessel, or may rely on the formation of a thrombus at the site of deployment of the device, in which case the device may substantially close the vessel or at least slow the flow of blood sufficiently to cause blood statis and thereby promote blood clotting.

A device which provides a total physical barrier across a vessel and thus instantaneous occlusion of the vessel can be particularly advantageous particularly when the vessel needs to be closed rapidly, for instance to perform another medical procedure or to stop blood loss from the vessel. However, these devices can be relatively difficult to deploy, typically not being suitable for delivery over a guide wire. Leaving any opening in the device for the passage of a guide wire can lead to loss of instantaneous occlusion and/or risk of leakage through the opening. For instance, a valve to close such an opening can lead to reduced compressibility for delivery purposes and is also liable to open or leak in use, thereby risking loss of occlusion function. Reliance on the creation of a thrombus to close the aperture, however small, fails to achieve instantaneous closure of the vessel, also is also at risk of recanalization.

A device which relies on causing thrombosis in the vessel can be designed for deployment over a guide wire, which can substantially facilitate the endoluminal delivery of the device into the vessel by providing a passage or lumen through the device for the guide wire. However, such devices occlude a vessel only over time, often taking hours. They can also be liable to recanalization over time.

Examples of mechanisms and devices for occluding or closing a vessel are described, for instance, in US-2008/0097509, U.S. Pat. No. 8,443,808 and U.S. Pat. No. 6,071,292.

SUMMARY OF THE PRESENT INVENTION

The present invention seeks to provide an improved implantable medical device and in the preferred embodiment an improved vascular occluder.

According to an aspect of the present invention, there is provided an implantable medical device including a tubular support element having first and second ends; and a sleeve having a lumen therein and a length, the sleeve being disposed within the tubular support element and extending between the first and second ends thereof; the sleeve being twisted along its length.

The twisting of the sleeve within the tubular support element causes the lumen of the sleeve to be twisted closed, which in practice will therefore close the passage through the device. However, it is still possible to pass an introducer assembly element through the sleeve, in particular a guide wire, enabling the device to be deployed over the wire, thereby benefitting from optimal deployment procedures. The twist of the sleeve will loosen when the device is radially compressed, as it is when held onto a carrier element of an introducer assembly, thereby opening the lumen in the sleeve and facilitating passage of a guide wire, for example, through the device. The twist will tighten when the device is allowed to expand off the carrier element and against the vessel wall, thereby closing the lumen. It is envisaged that the structure could be designed still to accommodate a guide wire, for instance in the sleeve when the device is expanded, so that the guide wire can be removed only after deployment of the device. On removal of the guide wire, blood pressure will impinge on the fabric of the sleeve, pushing this closed. The structure also avoids the risk of recanalization of the vessel. These characteristics are described in detail below.

Advantageously, the sleeve is twisted by at least 360 degrees between the first and second ends of the support element, in the preferred embodiments by at least 720 degrees. A twist of such degree will ensure closure of the lumen in the sleeve during use. It is possible to have a lower sleeve twist, for instance of around 180 or 270 degrees.

In the preferred embodiment, the sleeve is formed of an occluding material, for instance an impermeable material. The sleeve could also be formed of a substantially impermeable material, that is a material which does permit some passage of fluid therethrough but provides a sufficient barrier to cause blood statis at the upstream end of the device and as a result promotion of thrombosis.

In a practical embodiment, the sleeve may be formed of any of: ultra-high molecular weight polyethylene, such as Dyneema™, expanded polytetrafluoroethylene (EPTFE).

The sleeve may be formed from one of: a woven material, a knitted material or a film material.

In another embodiment, the sleeve is formed of a filtering material, for example a mesh or loosely woven, knitted or braided fabric. In this embodiment the device would act as a vascular filter rather than an occluder.

Advantageously, the tubular support element has a length, the sleeve having between the first and second ends of the support element a length greater than the length of the support element. The length of sleeve between the first and second ends of the support element may be at least 5 percent greater than the length of the support element, preferably at least 15 percent greater, more preferably least 25 percent greater. The greater length of the sleeve relative to the support element provides a certain looseness of the sleeve in the support, which can enhance the closing effect when blood pressure impinges on the twisted sleeve.

In one example, for a support element having a length of 20 millimeters, the sleeve 30 could have an overall length of 34 millimeters, with 3 millimeters at each end 32, 34 of the sleeve 30 being folded over the support ends 18, 20.

In a practical embodiment, the sleeve ends are wrapped over respective ends of the tubular support element. The wrapped sleeve ends may be bonded to the sleeve or to the support element. In another embodiment, the sleeve is disposed entirely within the frame and first and second annular strips are disposed at the ends of the sleeve and heat or chemically bonded to the sleeve so as to secure the sleeve to the frame.

Advantageously, the tubular support element is a stent. It may be made of self-expanding material, for example a spring material or a shape memory material.

Other features and advantageous of the invention taught herein will be apparent from the following description and accompanying drawings.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

The preferred embodiment described below is configured as a vascular occluder. It is to be understood, though, that the medical device could be configured to perform other functions, such as a vascular filter.

Figure 1:
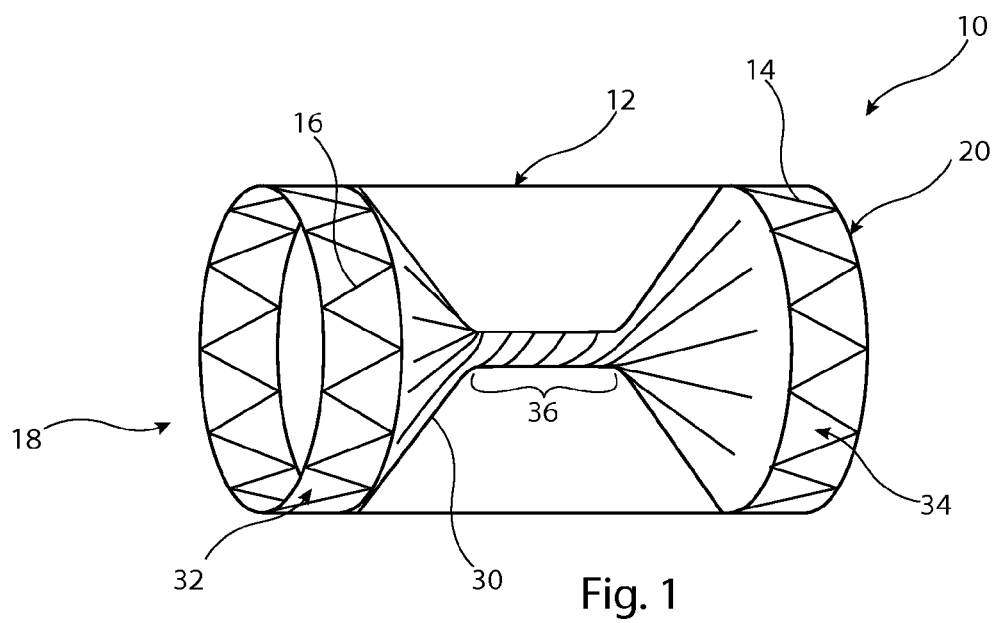
FIG. 1 is a side elevational view of a preferred embodiment of implantable vascular occluder according to the teachings herein.

Referring first to FIG. 1, this shows an implantable medical device 10 in the form, in this embodiment, of a vascular occluder. The device 10 includes a tubular support element 12 which in this embodiment is a stent formed of a plurality of zigzag stent rings 14 coupled together by a series of tie bars 16 connected in this example to apices or troughs of adjacent stent rings 14. The support element 12 is substantially cylindrical and round in transverse cross-section, although in other embodiments could have a different shape, for instance a tapering form or with a central waist. It is to be appreciated that stent rings 14 could extend for the whole length of the tubular support element 12, that is also with stent rings located between the end stents which are shown in the Figures. These intermediate stents are, in this embodiment, omitted solely for the sake of clarity and specifically to enable a better view of the sleeve 30. The support element 12 in this embodiment could be the applicant's Zilver™ stent.

At the ends 18 and 20 of the support element 12 there may be provided radiopaque markers 22 (shown in FIG. 2), for example disks of gold fixed into associated rings integral with the stent ends. Radiopaque markers of this type are known in the art.

The support element 12 is preferably made of a self-expanding material such as spring steel or a shape memory material such as a shape memory alloy. Nitinol or cobalt chromium alloy are suitable.

The device 10 also includes a sleeve 30 disposed within the internal lumen of the tubular support element 12 and having sleeve ends 32 and 34 which in this embodiment are wrapped over and to the outside of the support ends 18, 20. The wrapped over sleeve ends 32 and 34 can usefully be bonded to the internal sleeve in the zone where they overlap, by suitable bonding material or fusion for instance, thereby fixing the sleeve 30 to the support element 12. In other embodiments, the sleeve ends 32, 34 could be sewn to the parts of the sleeve they overlap or could be attached directly to the frame of the support element 12, for instance to the stent rings 14, by sutures or the like.

In another embodiment, the sleeve 30 is disposed entirely within the frame of the support element 12 with its ends adjacent the ends of the support element 12. First and second annular strips are disposed on the outside of the frame adjacent the ends of the sleeve 30 and heat or chemically bonded to the sleeve so as to secure the sleeve to the frame.

The sleeve in this embodiment is made of an effectively impermeable material such as ultra-high molecular weight polyethylene, for instance Dyneema™ or expanded polytetrafluoroethylene (EPTFE), polyester or any other known or suitable graft material. The material is preferably non-elastic but in some embodiments could be of elastic material, for instance having a maximum expansion of 5% at operational stresses. The sleeve 30 may allow a small amount of liquid to flow through it but acts as an effective barrier to blood flow, which will cause rapid coagulation of blood and as a result an occlusion of the vessel. The sleeve 30 can therefore be made of a material which is not completely impermeable but which is slightly permeable, that is of a nature and structure that it will provide a sufficient barrier to blood flow to cause blood statis at the location of the device 10 and as a result the formation of thrombi which will occlude the vessel. In other embodiments the sleeve is of a material which is impermeable and can provide total and instantaneous occlusion of the vessel.

The sleeve 30 could be made of woven or knitted material, or even sheet material. As will be apparent, the sleeve 30 is made of a thin sheet of material which is flexible so as to be turned into a sleeve and readily twisted on itself by a number of turns.

As will be apparent in FIG. 1, the sleeve is twisted along its length, causing it to constrict at location 36, typically around the midpoint along the supporting stent 12. This twist can be achieved by rotating the ends 32, 34 of the sleeve relative to one another during the fitting of the sleeve 30 to the support element 12. Typically, the ends will be rotated at least 360 degrees from one another, preferably 720 degrees or more. As will be apparent form a view of FIG. 1, the constriction zone 36 has a substantial length, which can ensure good occlusion of the lumen through the sleeve 30 and can be more effective than a short occluding barrier.

The sleeve 30 preferably has a diameter about the same as the diameter of the tubular support 12, although in some embodiments could be slightly larger. On the other hand, the length of the sleeve 30 extending within the tubular support 12 between its ends 18 and 20 is preferably longer than the length of the support 12, preferably at least 5 percent longer and in the preferred embodiments around 15 percent longer or more. In another embodiment shown in FIG. 4, then sleeve 30 could be longer, for instance having a length up to around 40% greater than that of the support 12 so as to sit loosely within the lumen of the tubular support 12, in which case the sleeve 30 could be turned by fewer degrees.

Figure 2:
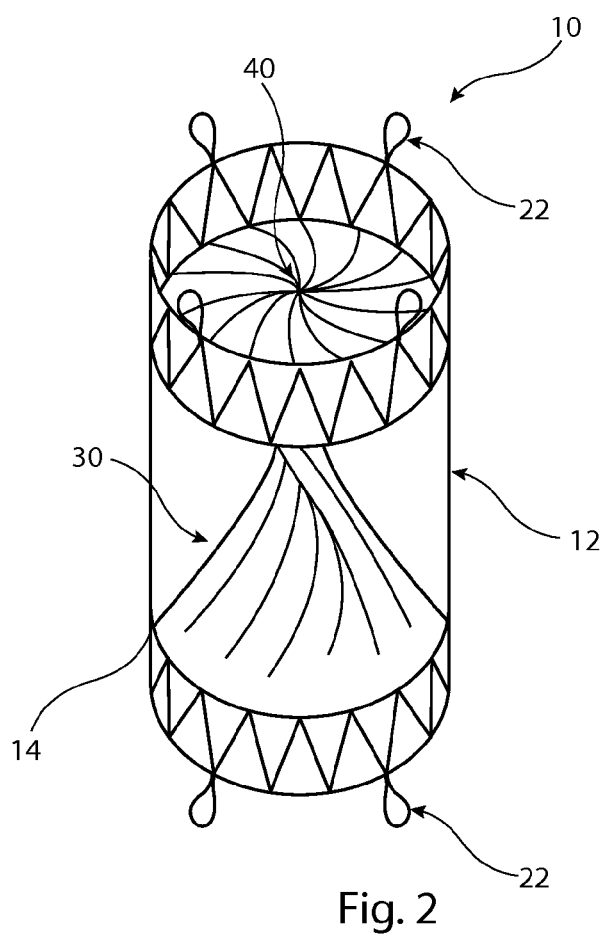
FIG. 2 is an end view of the occluder of FIG. 1.

Referring now to FIG. 2, this shows an end view of the device 10 of FIG. 1 and in particular the view through the lumen 40 of the sleeve 30. As can be seen, as a result of the twist of the sleeve between its two ends 32 and 34, the lumen is twisted closed. Moreover, as a result of the extra length of sleeve 30 relative to the length of the support element 12, the sleeve material is able to gather together at the point of twist, that is at the waist produced by the twist, which will enhance the closure of the lumen 40. The sleeve material will be caused to gather together particularly form the pressure of blood in the vessel, causing the material to push against itself. Specifically, the pressure of blood against the upstream facing sleeve end 32 or 34 will push back the material of the sleeve in a downstream direction, thereby compressing the material at the location of its waist. Furthermore, the blood pressure will create a parting force on the wall of the sleeve at the opening of the device 10 will act to tighten the twisted part of the sleeve. Thus, blood pressure will act to maintain closing pressure on the sleeve, thereby avoiding or reducing the risk of recanalization.

On the other hand, the degree of twist of the sleeve 30 is not so much as to prevent any passage through the lumen of the sleeve and in particular is such that an elongate element such as a guide wire or cannula can be kept in the lumen 40 of the sleeve. Moreover, when the support element 12 is radially compressed, for instance when loaded onto an introducer assembly, the radial compression thereof will loosen any radial tightening of the sleeve 30, allowing further opening of the lumen 40 by an elongate element of the type described.

Figure 3:
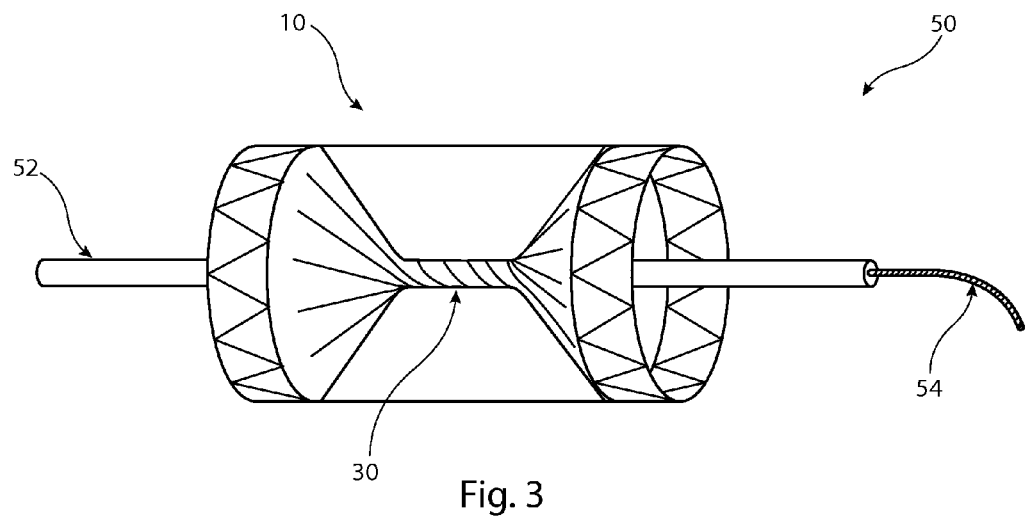
FIG. 3 is a perspective view of the occluder mounted on a carrier element of an introducer assembly.

FIG. 3 shows the device 10 fitted onto the distal end 50 of an introducer assembly of conventional form. The skilled person will be familiar with the structure and components of such an introducer assembly and therefore no detailed description thereof is provided herein.

The skilled person will appreciate from the teachings herein that the device 10 can be implanted either way around in a vessel as it has a symmetrical form.

The introducer assembly includes a tubular device carrier 52, such as a cannula or catheter, on which the medical device 10 can be held in radially compressed form. The carrier 52 in this embodiment includes a lumen therein for the passage of a guide wire 54. The medical device 10 in many instances can be kept radially compressed on the carrier 52 for delivery purposes by an outer sheath of the type commonly used in introducer assemblies. For this purpose, the introducer assembly may include a pusher element for pushing the device 10 out of the distal end of the sheath. In other embodiments carrier 52 may include device constraining elements, for instance restraining wires, restraining sleeves, cups or the like.

The lumen 40 of the sleeve 30, as explained, allows the passage therethrough of the carrier element 52, particularly when the device 10 is radially constrained, thereby to loosening the sleeve 30 radially. In some embodiments at least, the carrier element 54 can fit within the lumen 40 of the sleeve 30 even when the device is radially expanded.

Once the distal end 50 of the introducer assembly has been positioned at the treatment site, the constraints on the device 10 can be released, in known manner, allowing the device 10 to expand to the vessel walls and the carrier 52 and guide wire 54 are then withdrawn. The device 10 will, in the preferred embodiment, provide instantaneous occlusion of the vessel by virtue of closure of the lumen 40 of the sleeve 30.

Figure 4:
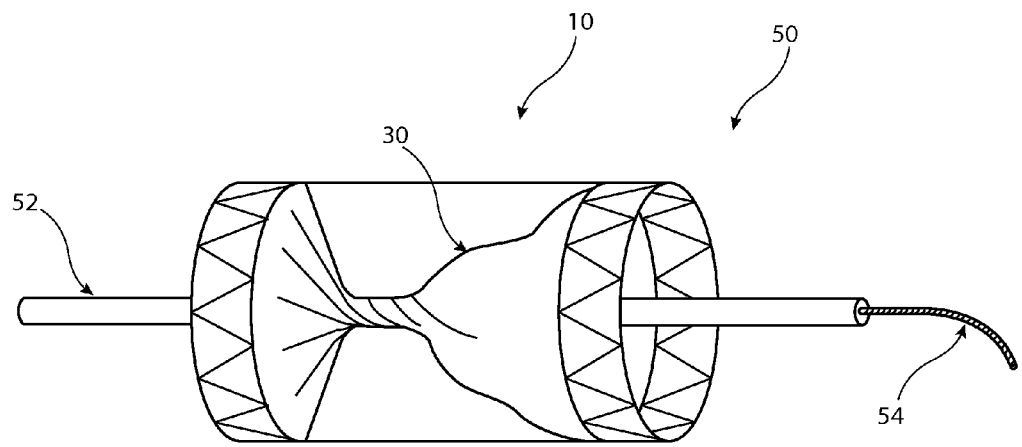
FIG. 4 is a view similar to FIG. 3 in which the occluder has a longer twisted sleeve.

Referring to FIG. 4, this shows another embodiment of occluder assembly 10 which includes a twisted sleeve 30 having a greater length within the length of the tubular support 12, in particular a length around 40% greater than that of the support 12. Having a longer sleeve leads to greater gathering of sleeve material at the point of the twist when implanted in a vessel. As a result, there is more material to fold and compress, leading to a potentially greater occluding barrier and the ability to reduce the degree by which the sleeve 30 is twisted in the support 12. However, having a greater amount of sleeve material in the support 12 can lead to reduced compressibility of delivery purposes.

The device 10 can be assembled on a guide wire catheter, so that the catheter is positioned within the sleeve before the latter is twisted and attached to the support frame 12. In this manner, the sleeve 30 can allow the passage of the guide wire catheter, until the latter is removed, whereupon the sleeve will completely close.

Figure 5:
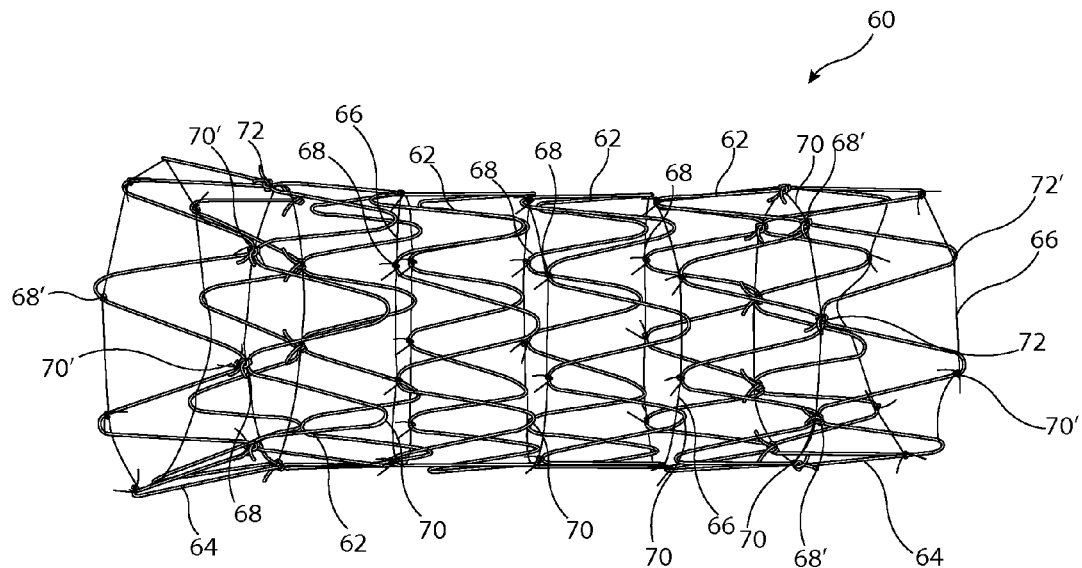
FIG. 5 is a side elevational view of an embodiment of tubular support frame for the occluder of FIG. 1.

Referring now to FIG. 5, this shows another embodiment of a tubular support element for use in an occluder according to the teachings herein. The tubular support element 60 is formed of a plurality of stent rings 62, 64 which are connected together by loops of suture thread 66. The stent rings 62, 64 comprise a series of what could be described as internal or intermediate stent rings 62 and two end stent rings 64. The stent rings 62, 64 could have precisely the same structures as one another. Differing only in the arrangement of stent rings relative to one another. The intermediate stent rings 62 are connected such that their apices 68 are aligned in the longitudinal direction of the element 60, as are their troughs 70. On the other hand, the end stents 64 are rotated relative to the intermediate stents 62 by half a period delimiting the zig-zag or wave shape of the stent rings, such that the troughs 70' are aligned with the peaks 68 of the adjacent intermediate stent ring 62 and are preferably tied together by a suture knot 72. Similarly, the peaks 78' are aligned with the troughs 70 of the adjacent stent (at the right of the view of FIG. 5) and equally tied by suture knots 72. As a result, the end stents 64 are relatively firmly attached to their adjacent intermediate stents 62, whereas the intermediate stents 62 are coupled to one another via the suture loops 66, with their respective peaks 68 and troughs 70 being connected via a length of suture thread. As a result, the support structure 60 is very flexible in its intermediate section and more rigid at its ends. The sleeve 30 is attached to the end stent 64, as per the embodiments depicted in FIGS. 1 to 4 and in the manner described above. This arrangement provides an occluder device which is very flexible in the longitudinal direction, enabling the device to curve within a curved vessel without imparting undue straightening forces on the vessel.

Figure 6:
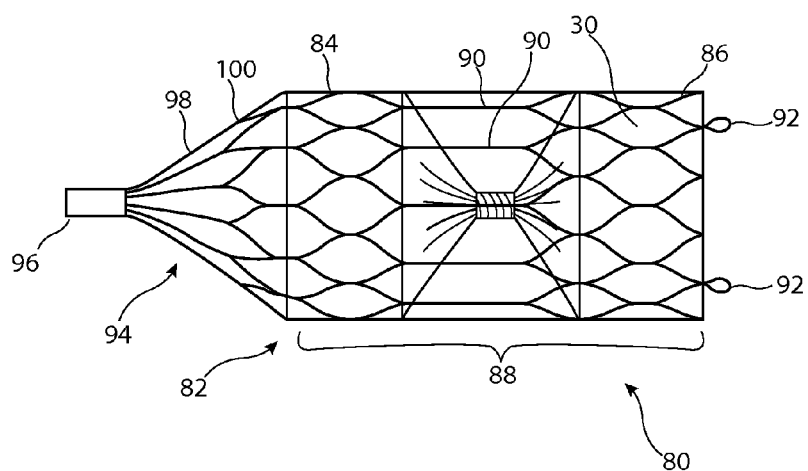
FIG. 6 is a side elevational view of another embodiment of occluder according to the teachings herein.

FIG. 6 shows another embodiment of implantable medical device 80, again configured in this embodiment as an occluder. The device 80 includes a frame 82 which has first and second stent structures 84, 86 either end of a tubular section 88 of the frame 82. The stent structures 84, 86 are formed of diamond shaped struts, in the embodiment shown being two rows of such diamond shaped struts. The stent structures 84, 86 are coupled together by longitudinally extending tie elements 90, which together circumscribe a cylindrical shape, such that the frame 82 could be said to be of tubular form overall.

At the extremity of the stent structure 86 there may be provided a plurality of radiopaque markers 92, of known form. Radiopaque markers may be provided in other locations in addition to or instead of those shown in FIG. 6.

The extremity of the stent structure 84 connects to a conical deployment and retrieval element 94 which in this embodiment comprises a tubular bushing 96 having a lumen passing longitudinally therethrough (the lumen not being visible in FIG. 6). Extending from the tubular coupling element 96 are a plurality of conically arranged struts 98 which connect to apices 100 of the diamond shaped strut arrangement on the stent structure 84. The retrieval/deployment element 94 assists in maintaining hold of the device 80 during the deployment operation, allowing the repositioning of the device 80 in case it is not positioned in the correct location within a patient's vessel. It can also act a convenient retrieval element for retrieving the occluder 80 from within the patient's vessel. The sleeve 96 can be attached to a retrieval hook or other device, with the conically arranged struts 98 being useful in compressing the frame 82 radially into a retrieval catheter, in a manner which will be appreciated by the person skilled in the art.

The sleeve 30 is connected and wound to the stent structures 84, 86 in a manner analogous to the embodiments described above.

The frame 82, including the sleeve 96 and conically arranged connecting struts 98 can usefully be used from a common tubing from which the diamond shaped stent strut structure, longitudinal tie bars 80 and strut elements 98 can usefully be cut, technically by a laser.

The conical end 94 of the frame does not impact on the functionality of the device given that this will occlude (and in other embodiments filter) the fluid in the vessel.

The structure 80 depicted in FIG. 6 is particularly useful for very small diameter vessels and introducer systems and can, for example, have a deployed diameter as small as 2 to 3 mm, deployable in an introducer system of around 4 French in diameter. It will be appreciated, of course, that the structure 80 can be useful in a large range of vessels by suitable scaling up. By contrast, the embodiments shown in FIGS. 1 to 5 can be used in larger vessel sizes, typically of between 3 and 12 mm in diameter or in even larger vessels.

The frame of all of the embodiments described above can usefully be made of shape memory material, preferably a shape memory alloy such as Nitinol. Other embodiments could use shape memory polymers and even spring materials such as spring steel or other resilient material.

It will be appreciated that the features of the various embodiments described can be combined and used in all of the embodiments. For example, the retrieval device 94 of the embodiment of FIG. 6 could be used also in the embodiments of FIGS. 1 to 5 and, could take other forms.

The skilled person will appreciate that it is not necessary for the support element 12 to be of the form shown in the drawings and could have other structures. Any structure which provides for radial expansion of the ends 32 and 34 of the sleeve 30 and which holds the ends at a given distance from one another can be used. For example, the support 12 could be a tube of sheet material, and could equally be in the form of a pair of radially expandable annular rings held spaced from one another by spacing rod or other element, for instance.

In other embodiments, the sleeve could be made of a filter material, such as a filter mesh.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1407686.3, from which this application claims priority, and in the abstract accompanying this application are incorporated herein by reference.

The invention claimed is:

1. An implantable medical device including a continuous tubular support element having a first end and a second end of the tubular support element; and a sleeve having a lumen therein and a length, the sleeve being disposed within the tubular support element and extending between the first and second ends thereof, a first end of the sleeve being fixed to the first end of the tubular support element and a second end of the sleeve being fixed to the second end of the tubular support element; the sleeve having a permanently twisted configuration along its length between the first end and the second end of the tubular support element the tubular support element remaining cylindrical while the sleeve is in said twisted configuration.

2. The implantable medical device according to claim 1, wherein the sleeve is twisted by at least 180 degrees between the first and second ends of the support element.

3. The implantable medical device according to claim 1, wherein the sleeve is formed from one of an occluding material and a substantially impermeable material.

4. The implantable medical device according to claim 1, wherein the sleeve is formed of any of: ultra-high molecular weight polyethylene, expanded polytetrafluoroethylene (EPTFE) or polyester.

5. The implantable medical device according to claim 1, wherein the sleeve is formed of a filtering material.

6. The implantable medical device according to claim 1, wherein the sleeve is formed from one of: a woven material, a knitted material and film material.

7. The implantable medical device according to claim 1, wherein the tubular support element has a length extending from the first end to the second end, and the length of the sleeve is greater than the length of the support element.

8. The implantable medical device according to claim 7, wherein the length of the sleeve is at least 5 percent greater than the length of the support element.

9. The implantable medical device according to claim 1, wherein each of the first and second sleeve ends is wrapped over a respective end of the tubular support element.

10. The implantable medical device according to claim 1, including a first annular band and a second annular band disposed at the first and second ends of the support element and bonded to the first and second sleeve ends.

11. The implantable medical device according to claim 9, wherein the first and second sleeve ends are bonded to the sleeve, to the annular bands or to the support element.

12. The implantable medical device according to claim 1, wherein the tubular support element is a stent composed of a plurality of adjacent stent rings tied to one another, the tubular support element, the sleeve extending through the stent and having a first sleeve end circumferentially affixed to a first stent ring of the plurality of stent rings and a second sleeve end circumferentially affixed to a second stent ring of the plurality of stent rings, wherein the sleeve is twisted by at least 360 degrees between the first and second sleeve ends.

13. The implantable medical device according to claim 1, wherein the tubular support element is made of self-expanding material.

14. The implantable medical device according to claim 1, wherein the tubular support element is made of a spring material or a shape memory material.

15. The implantable medical device according to claim 1, wherein the tubular support includes a first end stent structure and a second end stent structure connected to one another by one or more longitudinally extending connecting members.

16. The implantable medical device according to claim 15, wherein the one or more longitudinally extending connecting members are a plurality of longitudinally extending connecting members circumferentially distributed around the end stent structures.

17. The implantable medical device according to claim 1, including a retrieval member connected to one end of the tubular support.

18. The implantable medical device according to claim 17, wherein the retrieval member includes a tubular coupling sleeve and a plurality of struts or tethers extending from the coupling sleeve to the tubular support element.

19. The implantable medical device according to claim 18, wherein the retrieval member and the tubular support are cut from a common tube.

\* \* \* \* \*